US011570988B2

(12) United States Patent
An et al.

(10) Patent No.: US 11,570,988 B2
(45) Date of Patent: Feb. 7, 2023

(54) SPORICIDAL METHODS AND COMPOSITIONS

(71) Applicant: EVONIK OPERATIONS GMBH, Essen (DE)

(72) Inventors: Weidong An, Williamsville, NY (US); Coryn Mittiga, Tonawanda, NY (US); Ricky Mittiga, Tonawanda, NY (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/428,216

(22) Filed: May 31, 2019

(65) Prior Publication Data

US 2019/0364892 A1   Dec. 5, 2019

Related U.S. Application Data

(60) Provisional application No. 62/678,562, filed on May 31, 2018.

(51) Int. Cl.
*A01N 37/16* (2006.01)
*A01N 59/00* (2006.01)
*A61L 2/18* (2006.01)

(52) U.S. Cl.
CPC ............. *A01N 37/16* (2013.01); *A01N 59/00* (2013.01); *A61L 2/186* (2013.01); *A61L 2202/24* (2013.01)

(58) Field of Classification Search
CPC ..................................... A01N 37/16
USPC ......................................... 424/616
See application file for complete search history.

(56) References Cited

U.S. PATENT DOCUMENTS

| | | |
|---|---|---|
| 4,022,605 A | 5/1977 | Konya et al. |
| 4,915,955 A | 4/1990 | Gomori |
| 5,439,663 A | 8/1995 | Manganaro et al. |
| 5,512,309 A | 4/1996 | Bender et al. |
| 5,632,676 A | 5/1997 | Kurschner et al. |
| 5,849,985 A | 12/1998 | Tieckelmann et al. |
| 5,879,653 A | 3/1999 | Castrantas et al. |
| 5,977,403 A | 11/1999 | Byers |
| 6,365,099 B1 | 4/2002 | Castrantas et al. |
| 6,534,075 B1 | 3/2003 | Hei |
| 6,828,294 B2 | 12/2004 | Kellar et al. |
| 7,347,647 B2 | 3/2008 | Seech et al. |
| 7,416,718 B2 | 8/2008 | Sethi et al. |
| 7,473,372 B2 | 1/2009 | Block et al. |
| 7,510,721 B2 | 3/2009 | Roden et al. |
| 7,524,141 B2 | 4/2009 | Sethi et al. |
| 7,547,430 B2 | 6/2009 | Sethi et al. |
| 7,576,254 B2 | 8/2009 | Block et al. |
| 7,666,315 B2 | 2/2010 | Lopez Martinez et al. |
| 7,785,038 B2 | 8/2010 | Block et al. |
| 7,947,745 B1 | 5/2011 | Laramay et al. |
| 7,998,446 B2 | 8/2011 | Pfeffer et al. |
| 8,029,693 B2 | 10/2011 | Dada et al. |
| 8,424,493 B2 | 4/2013 | Hilgren et al. |
| 8,454,890 B2 | 6/2013 | Rovison, Jr. et al. |
| 8,486,366 B2 | 7/2013 | Pfeffer et al. |
| 8,575,075 B2 | 11/2013 | Huang et al. |
| 8,865,066 B2 | 10/2014 | Rovison et al. |
| 8,877,149 B2 | 11/2014 | Pfeffer et al. |
| 9,005,669 B2 | 4/2015 | Allen et al. |
| 9,018,142 B2 | 4/2015 | Rovison, Jr. et al. |
| 9,114,357 B2 | 8/2015 | Block et al. |
| 9,242,879 B2 | 1/2016 | Keasler et al. |
| 9,254,400 B2 | 2/2016 | Hilgren et al. |
| 9,295,744 B2 | 3/2016 | Rovison et al. |
| 9,351,488 B2 | 5/2016 | Rovison et al. |
| 9,375,768 B2 | 6/2016 | Pisanova et al. |
| 9,656,890 B2 | 5/2017 | Block |
| 9,821,353 B2 | 11/2017 | Pisanova et al. |
| 9,849,203 B2 | 12/2017 | Rovison, Jr. et al. |
| 9,986,737 B2 | 6/2018 | Rovison et al. |
| 10,344,199 B2 | 7/2019 | Pisanova et al. |
| 10,625,655 B2 | 4/2020 | Rovison, Jr. et al. |
| 2002/0110602 A1 | 8/2002 | Sorenson |
| 2008/0226541 A1 | 9/2008 | Zhou et al. |
| 2010/0196503 A1 | 8/2010 | Heisig et al. |
| 2012/0189494 A1 | 7/2012 | Rovison, Jr. et al. |
| 2014/0134047 A1 | 5/2014 | Herdt et al. |
| 2014/0228328 A1 | 8/2014 | Rovison et al. |
| 2015/0005379 A1 | 1/2015 | Block et al. |
| 2015/0141301 A1 | 5/2015 | Rovison, Jr. et al. |

(Continued)

FOREIGN PATENT DOCUMENTS

| | | |
|---|---|---|
| CA | 2944237 | 11/2015 |
| EP | 0411970 | 2/1991 |

(Continued)

OTHER PUBLICATIONS

Leggett, M. J. et al., "Mechanism of Sporicidal Activity for the Synergistic Combination of peracetic acid and hydrogen peroxide," Applied and Environmental Microbiology, Feb. 2016, vol. 82, No. 4, pp. 1035-1039.
International Search Report and Written Opinion dated Sep. 20, 2019 in corresponding PCT Application No. PCT/US2019/034923.
International Preliminary Report on Patentability for corresponding PCT application PCT/US2019/034923 filed May 31, 2019.
International Search Report for PCT/US2019/038457 filed Jun. 21, 2019, which corresponds to copending U.S. Appl. No. 16/448,542.
Written Opinion of the International Searching Authority for PCT/US2019/038457 filed Jun. 21, 2019, which corresponds to copending U.S. Appl. No. 16/448,542.

*Primary Examiner* — Sarah Alawadi
(74) *Attorney, Agent, or Firm* — Law Office of Michael A. Sanzo, LLC (57) ABSTRACT

Provided herein are methods and compositions for the reduction of endospore contamination of a substrate with percarboxylic acid-based compositions. The methods can include the step of continuously monitoring the oxidation-reduction potential of the percarboxylic acid-based compositions.

20 Claims, 6 Drawing Sheets

(56) References Cited

U.S. PATENT DOCUMENTS

| | | |
|---|---|---|
| 2015/0208648 A1 | 7/2015 | Iwashita et al. |
| 2015/0218437 A1 | 8/2015 | Rovison, Jr. et al. |
| 2015/0239738 A1 | 8/2015 | Zhou et al. |
| 2015/0258589 A1 | 9/2015 | Seech |
| 2015/0305342 A1 | 10/2015 | Burke et al. |
| 2016/0183522 A1 | 6/2016 | Rovison et al. |
| 2016/0345576 A1 | 12/2016 | Rovison et al. |
| 2017/0313604 A1 | 11/2017 | Garibi et al. |
| 2018/0065874 A1 | 3/2018 | Au et al. |
| 2018/0103638 A1 | 4/2018 | Puente de Vera et al. |
| 2018/0117198 A1 | 5/2018 | Rovison, Jr. et al. |
| 2018/0271090 A1 | 9/2018 | Rovison et al. |
| 2018/0360060 A1 | 12/2018 | Pisanova et al. |
| 2019/0144313 A1 | 5/2019 | Block et al. |
| 2019/0152817 A1 | 5/2019 | Block et al. |
| 2019/0248679 A1 | 8/2019 | Rovison et al. |
| 2019/0380337 A1 | 12/2019 | Mittiga et al. |
| 2019/0388574 A1 | 12/2019 | An et al. |
| 2020/0238887 A1 | 7/2020 | Rovison, Jr. et al. |
| 2020/0352165 A1 | 11/2020 | Puente de Vera et al. |
| 2021/0253454 A1 | 8/2021 | Mittiga |

FOREIGN PATENT DOCUMENTS

| | | | |
|---|---|---|---|
| JP | 2012219053 A | * | 4/2011 |
| JP | 2014-014801 | | 1/2014 |
| JP | 2015-187084 | | 10/2015 |
| WO | 01/70030 | | 9/2001 |
| WO | WO2017100284 | * | 12/2016 |

OTHER PUBLICATIONS

International Preliminary Report on Patentability for PCT/US2019/038457 filed Jun. 21, 2019, which corresponds to copending U.S. Appl. No. 16/448,542.

International Search Report for PCT/US2018/037805 filed Jun. 15, 2018, which corresponds to copending U.S. Appl. No. 16/009,936.

Written Opinion of the International Searching Authority for PCT/US2018/037805 filed Jun. 15, 2018, which corresponds to copending U.S. Appl. No. 16/009,936.

International Preliminary Report on Patentability for PCT/US2018/037805 filed Jun. 15, 2018, which corresponds to copending U.S. Appl. No. 16/009,936.

Bell, et al., "Reduction of foodborne micro-organisms on beef carcass tissue using acetic acid, sodium bicarbonate and hydrogen peroxide spray washes," *Food Microbiology* 14:439-448 (1997).

Lee, et al., "Development of Environmental-friendly Cleaning Agents Utilizing Organic Acids for Removal of Scale on the Wall of Cleaning Beds and Distribution Reservoirs in the Waterworks," *Clean Technology* 18(3):272-279 (Sep. 2012).

Sen, et al., "Effect of chilling, polyphosphate and bicarbonate on quality characteristics of broiler breast meat," *British Poultry Science* 46(4):451-456 (2005).

U.S. Appl. No. 16/009,936 , filed Jun. 15, 2018, US-2018/0360060 A1, Dec. 20, 2018, Pisanova.

U.S. Appl. No. 16/191,757, filed Nov. 15, 2018, US-2019/0144313 A1, May 16, 2019, Block.

U.S. Appl. No. 16/194,559, filed Nov. 19, 2018, US-2019-0152817 A1, May 23, 2019, Block.

U.S. Appl. No. 16/275,894, filed Feb. 14, 2019, US-2019-0248679 A1, Aug. 15, 2019, Rovison.

U.S. Appl. No. 16/448,542, filed Jun. 21, 2019, US-2019-0388574 A1, Dec. 26, 2019, An.

U.S. Appl. No. 16/777,057, filed Jan. 30, 2020, US-2020-0238887 A1, Jul. 30, 2020, Rovison.

U.S. Appl. No. 16/936,663, filed Jul. 23, 2020, US-2020-0352165 A1, Nov. 12, 2020, Puente de Vera.

U.S. Appl. No. 17/253,953, filed Dec. 18, 2020, Mittiga.

Abadias, et al., "Evaluation of alternate sanitizers to chlorine disinfection for reducing foodborne pathogens in fresh-cut apple," *Postharvest Biology and Technology* 59(3):289-297 (Mar. 2011).

Walter, et al., "Efficacy of sodium hypochlorite and peracetic acid in sanitizing green coconuts," *Letters in Applied Microbiology* 49(3):366-371 (Sep. 2009).

* cited by examiner

Figure 6

SPORICIDAL METHODS AND COMPOSITIONS

CROSS REFERENCE TO RELATED APPLICATIONS

This application claims priority under 35 U.S.C. § 119(e)(1) from U.S. Provisional Application Ser. No. 62/678,562, filed May 31, 2018, the contents of which are incorporated herein by reference.

FIELD OF THE INVENTION

The present invention relates to percarboxylic acid-based compositions for reducing endospore contamination.

BACKGROUND OF THE INVENTION

Certain species of bacteria can form endospores in response to harsh conditions or nutrient deprivation. Endospores are dormant, multi-layered non-reproductive structures containing highly compacted microbial DNA. Endospores are resistant to environmental insults, for example, high temperature, UV irradiation, desiccation, chemical and enzymatic exposure that would normally kill the bacterium. As a result, endospores are not readily killed by standard antimicrobial treatments. Upon exposure to suitable conditions such as heat and nutrient media, endospores can germinate to produce viable bacteria. Endospores can remain dormant for extended periods. Human pathogens such as *Bacillis anthracis* and *Clostridium botulinum* are spore-forming bacteria. Endospore contamination, for example, contamination of medical equipment, equipment used in pharmaceutical manufacturing and in food packaging, as well as of the foodstuffs themselves, can pose a significant risk to human health. There is a continuing need for methods that safely and effectively eliminate contamination with endospores and endospore forming microbes.

SUMMARY OF THE INVENTION

Provided herein are methods of reducing contamination of a substrate by endospores or sporulating microorganisms, the method including contacting the substrate with composition comprising a percarboxylic acid and hydrogen peroxide at a weight percent ratio of between about 1.2 and 30.0 in the absence of a peroxide decomposing enzyme, for a time sufficient to reduce the contamination. The endospores can be produced by a microbe selected from the group consisting of *Paenibacillus chibensis, Paenibacillus favisporus, Bacillus cereus, Bacillus atrophaeus, Bacillus subtilis,* and *Geobacillus stearothermophilus* or a combination thereof. The percarboxylic acid can include a $C_1$-$C_{10}$ percarboxylic acid, for example, peracetic acid. The weight percent ratio of percarboxylic acid to hydrogen peroxide can be about 1.2, 1.6, 1.8, 2.0, 2.2, 2.4, 2.5, 2.6, 2.8, 3.0, 3.2, 3.4, 3.6, 3.8, 4.0, 4.2, 4.4, 4.6, 4.8, 5.0, 5.2, 5.4, 5.6, 5.8, or 6.0. Also provided are methods of reducing contamination of a substrate by endospores or sporulating microorganisms, the method including contacting the substrate with a composition comprising a percarboxylic acid and hydrogen peroxide having an oxidation-reduction potential (ORP) of greater than about 500 mV, in the absence of a peroxide decomposing enzyme, for a time sufficient to reduce the contamination. Also provided is a method of treating a substrate contaminated with or at risk for endospore contamination, the method including the steps of preparing a solution comprising percarboxylic acid and hydrogen peroxide; adjusting the concentration of the percarboxylic acid and hydrogen peroxide to provide an oxidation-reduction potential (ORP) of greater than 500 mV; and contacting the substrate with the adjusted solution in the absence of a peroxide decomposing enzyme for a time sufficient to reduce the endospore contamination, wherein the ORP is continuously monitored during the contacting step.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENT

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

The present invention is directed to methods and compositions for reducing endospore contamination of a substrate. The inventors have found that a composition comprising a percarboxylic acid and hydrogen peroxide at a weight percent ratio of between about 1.2 and 6.0 in the absence of a peroxide decomposing enzyme effectively reduced endospore contamination. More specifically, the weight percent ratio of between about 1.2 and 6.0 in the absence of a peroxide decomposing enzyme provided a substantial reduction in the level of endospore forming microbes in shorter contact times than those obtained with a weight percent ratio below about 1.2. The compositions showed sporicidal activity against microbes that are generally resistant to standard antimicrobial treatment.

The inventors also found that the oxidation reduction potential (ORP) of the peracetic acid/hydrogen peroxide ($PAA/H_2O_2$) solutions increased with increasing PAA concentration. Unexpectedly, the ORP, and thus the oxidizing power, of the solution increased as the $PAA/H_2O_2$ ratio increased, even when the PAA concentration was held constant. Conversely, increasing the amount of $H_2O_2$ when the PAA concentration was held constant reduced the ORP, and thus the oxidizing power of the solution, even though $H_2O_2$ is generally considered to be a strong oxidant. Accordingly, systems for sporicidal treatment based on continuous monitoring of ORP are provided.

Without being limited to any particular theory, it appears that the relationship between ORP and $PAA/H_2O_2$ ratios relates to the dual role played by $H_2O_2$ in peracid-based formulations in which $H_2O_2$ can serve as either an oxidizer or a reducer.

Compositions

The compositions disclosed herein include a percarboxylic acid. Percarboxylic acids can include organic aliphatic peracids having 2 or 3 carbon atoms, e.g., peracetic acid and peroxypropanoic acid. Percarboxylic acids can include the $C_1$-$C_{10}$ carboxylic peracids. Other percarboxylic acids can include the $C_2$-$C_5$ dicarboxylic peracids or $C_6$-$C_{12}$ monocarboxylic peracids. Additional peracids are lower organic aliphatic monocarboxylic acid having 2-5 carbon atoms, such as acetic acid (ethanoic acid), propionic acid (propanoic acid), butyric acid (butanoic acid), iso-butyric acid (2-methyl-propanoic acid), valeric acid (pentanoic acid), 2-methyl-butanoic acid, iso-valeric acid (3-methyl-butanoic) and 2,2-dimethyl-propanoic acid.

Useful peracids for the methods disclosed herein are peracetic acid (peroxyacetic acid or PAA) or performic acid, or a combination thereof. Percarboxylic acid solutions, for example, peracetic acid solutions, typically are dynamic equilibrium mixtures of peracetic acid, water, hydrogen peroxide, acetic acid and water. The weight ratios of these compounds can vary. Useful weight ratios of peracetic acid/hydrogen peroxide ($PAA/H_2O_2$) can range from about 1.2 to about 30.0. Thus, the weight ratio of $PAA/H_2O_2$ can be about 1.2, about 1.6, about 1.8, about 2.0, about 2.2, about 2.4, about 2.5, about 2.6, about 2.8, about 3.0, about 3.2, about 3.4, about 3.6, that 3.8, about 4.0, about 4.2, about 4.4, about 4.6, about 4.8, about 5.0, about 5.2, about 5.4, about 5.6, about 5.8, about 6.0, about 6.5, about 7.0, about 7.5, about 8.0, about 8.5, about 9.0, about 9.5, about 10.0, about 12.0, about 14.0, about 16.0, about 18.0, about 20.0, about 22.0, about 24.0, about 26.0, about 28.0, or about 30.0. In some embodiments, the weight ratio of $PAA/H_2O_2$ can be about 1.5, about 2.2, about 5.0 or about 5.5.

Peracetic acid solutions can be identified by the concentration of peracetic acid and hydrogen peroxide. Commercially available peracetic acid solutions have typical formulations containing 2-35% peracetic acid and 5-30% hydrogen peroxide, with the remainder being acetic acid and water. Exemplary peracetic acid solutions can include 15% peracetic acid with 10% hydrogen peroxide; 22% peracetic acid with 10% hydrogen peroxide; 35% peracetic acid with 7% hydrogen peroxide; 15% peracetic acid with 3% hydrogen peroxide; 22% peracetic acid with 4% hydrogen peroxide Exemplary PAA solutions are those having weight ratios of PAA:hydrogen peroxide:acetic acid from 15:10:36; 15:10:35; 35:10:15; 20-23:5-10:30-45 and 35:10:15.

The concentration of the peracetic acid in the compositions can range from about 1 ppm to about 10,000 ppm. Thus the concentration of the peracetic acid can be about 1 ppm, about 2 ppm, about 3 ppm, about 4 ppm, about 5 ppm, about 6 ppm, about 7 ppm, about 8 ppm, about 9 ppm, about 10 ppm, about 12 ppm, about 15 ppm, about 18 ppm, about 20 ppm, about 25 ppm, about 30 ppm, about 35 ppm, about 40 ppm, about 45 ppm, about 50 ppm, about 60 ppm, about 75 ppm, about 100 ppm, about 125 ppm, about 150 ppm, about 200 ppm, about 250 ppm, about 300 ppm, about 350 ppm, about 400 ppm, about 450 ppm, about 500 ppm, about 1000 ppm, about 1500 ppm, about 2000 ppm, about 2200 ppm, about 2500 ppm, about 2900 ppm, about 3000 ppm, about 3500 ppm, about 4000 ppm, about 4500 ppm, about 5000 ppm, about 6000 ppm, about 7500 ppm, or about 10,000 ppm.

Peroxides can be obtained as aqueous stock solutions and diluted for use. Aqueous hydrogen peroxide stock solutions can contain at least about 8 wt % $H_2O_2$, at least about 15 wt % $H_2O_2$, at least about 20 wt % $H_2O_2$, at least about 27% $H_2O_2$, at least about 35 wt % $H_2O_2$. Aqueous hydrogen peroxide stock solutions with these concentrations, suitable for use in the invention, are readily available from commercial suppliers as stabilized $H_2O_2$ solutions. Highly concentrated aqueous hydrogen peroxide stock solutions (significantly above 50 wt % $H_2O_2$) can also be used. Aqueous $H_2O_2$ stock solutions above about 50 wt % $H_2O_2$ generally require stringent handling and safety measures. Thus, the aqueous hydrogen peroxide stock solutions can have a concentration in the range of about 8 wt % $H_2O_2$ to about 70 wt % $H_2O_2$, about 15 wt % $H_2O_2$ to about 50 wt % $H_2O_2$, about 25 wt % $H_2O_2$ to about 40 wt % $H_2O_2$. Useful stock solutions can have a concentration in the range about 30 wt % $H_2O_2$ to about 40 wt $H_2O_2$.

The compositions disclosed herein exclude a peroxide decomposing enzyme, for example, a catalase. Such enzymes catalyze the decomposition of peroxide into water and oxygen. The inventors have found that contrary to previous teachings which relied upon catalase treatment to reduce levels of peroxide in $PAA/H_2O_2$ compositions to enhance efficacy, $PAA/H_2O_2$ compositions at a weight percent ratio of between about 1.2 and 6.0 provided effective sporicidal activity in the absence of catalase. Thus, the omission of catalase provides effective sporicidal activity without the cost and without the need to further treat the samples to remove residual enzyme.

The compositions disclosed herein exclude a peroxide sequestering agent, that is, an agent that can form a complex with peroxide such that the activity of the peroxide is abrogated. A peroxide sequestering agent can be, for example, a salt of titanium (IV) such as titanium acetate.

The compositions can include or exclude an adjuvant. An adjuvant can be a stabilizer, a wetting agent, or a reagent that enhances the biocidal activity of the composition. In some embodiments, the adjuvant can be an acid, for example sulfuric acid ($H_2SO_4$). In some embodiments, an adjuvant can be a hydroxy acid, such as citric acid, isocitric acid, lactic acid, gluconic acid, and malic acid. In some embodiments, an adjuvant be a metal chelator, for example ethylenediaminetetraacetic acid (EDTA). In some embodiments, an adjuvant can be a stabilizer, for example, a phosphonic acid or phosphonate, for example, DeQuest 2010. In some embodiments, an adjuvant can be a sequestrant, for example, dipicolinic acid. In some embodiments, an adjuvant can be a surfactant, for example, an anionic laurylate, a sorbitan and its respective esters, i.e. polyethylene sorbitan monolaurylate; and a short chain fatty ester (C6-C12).

The compositions disclosed herein are generally and variously useful for treatment of substrates that are contaminated with a sporulating microorganism or are at risk for contamination or suspected of being contaminated with a sporulating microorganism. The compositions can be formulated in a variety of ways. In one embodiment, percarboxylic acid and hydrogen peroxide can be combined prior to use to form a concentrated aqueous solution. The concentrated aqueous solution can be diluted just prior to use the appropriate concentration. The oxidizing power of the solution can be monitored continuously by assessing the oxidation-reduction potential. The oxidation reduction potential can be monitored using one or more ORP probes. In general, useful ORP values will be about 450 mV, about 480 mV, about 500 mV, about 520 mV, about 540 mV, about 560 mV, about 580 mV, about 600 mV, about 620 mV, about 640 mV, about 660 mV, about 680 mV, about 700 mV, about 720 mV, about 740 mV, about 760 mV, about 780 mV, about 800 mV, about 820 mV, about 840 mV, about 860 mV, about 880 mV, about 900 mV, about 920 mV, about 940 mV, about 960 mV, about 980 mV, or about 1000 mV.

The diluted aqueous solution can be applied to the substrate as a liquid or ice, mist, fog, vapor or supercritical fluid. The substrate can be contacted by the compositions in a variety of ways, including, for example by dipping, flooding, immersing, or spraying as a mist or a fog. Alternatively, the compositions can be evaporated into a gaseous vapor and applied as a vapor. In some embodiments, a concentrated aqueous solution can be added to the water in a tank to arrive at a final concentration suitable for antimicrobial treatment.

The contact time between the compositions and the substrate can vary depending upon the temperature, the nature of the substrate, the method of application, and the particular microorganism being targeted. The contact time between the compositions and the substrate can range from a few seconds to more than one hour. Exemplary contact times include about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 40 seconds, about 45 seconds, about 50 seconds, about 60 seconds, about 90 seconds, about 120 seconds, about 3 minutes, about 5 minutes, about 8 minutes, about 10 minutes, about 15 minutes, about 30 minutes, about 45 minutes, or about 60 minutes.

In general, a reduction of microbial contamination can be assayed by determining the level of viable microbes on the treated substrate. In some embodiments, a reduction of microbial contamination can be a reduction of about 50%, about 80% about 90%, about 95%, about 99% or about 99.9% of the contamination of the treated food product compared to an untreated control substrate. Alternatively, or in addition, the reduction can be specified as a $Log_{10}$ reduction. Thus in some embodiments, a reduction of microbial contamination can be a 1, 2, 3, 4, 5, 6, or 7 Log reduction relative to an untreated control substrate. Levels of microbial contamination can be determined, for example, by standard cultural methods involving microbial outgrowth, nucleic acid amplification techniques such as polymerase chain reaction, and immunoassays.

In some embodiments, efficacy of treatment can be expressed as the "D-value." The D-value is the time (e.g., seconds) needed for achieving a 1 $Log_{10}$ (or 90%) reduction of the target organism at the given temperature and PAA concentration. So, the smaller the D-value, the higher the antimicrobial efficacy.

The methods and compositions disclosed herein are useful for reducing contamination by spore forming bacteria, including both anaerobic and aerobic spore forming organisms. Exemplary anaerobic organisms include *Clostridium* spp., for example, *Clostridium botulinum* and *Clostridium perfringens*. Exemplary aerobic organisms include *Paenibacillus* spp, for example, *Paenibacillus chibensis* and *Paenibacillus favisporus; Geobacillus* spp., for example *Geobacillus stearothermophilus; Bacillus* spp., for example, *Bacillus cereus, Bacillus atrophaeus, Bacillus subtilis; Brevibacillus* spp., for example, *Brevibacillus agri* and *Brevibacillus borstelensis; Sporosarcina* spp., for example, *Sporosarcina ureae*; and *Paenisporosarcina*.

The compositions can be used applied to a variety of substrates comprising a variety of materials including, medical, plastic, ceramic glass, wood, rubber composite or a combination thereof. The substrate can be a substrate that contaminated with a spore forming microbe or a substrate that is vulnerable to or at risk for contamination by a spore forming microbe. For example, the compositions can be applied to a substrate comprising a medical device, food or beverage preparation equipment, pharmaceutical manufacturing equipment, or a foodstuff. Exemplary substrates include equipment and packaging used in food preparation and processing, for example, beverage containers, aseptic filling machines, dairy equipment; equipment and containers used in pharmaceutical preparation and packaging, medical equipment and devices, such as surgical instruments or other instruments used in diagnosis, for example endoscopes dental tools and other equipment, and veterinary equipment.

The compositions can be applied to a wide variety of objects including buildings and their contents. Thus, the compositions may be applied to floors, walls, doors, door handles and fixtures in any of the facilities described above. The compositions may also be applied to objects found in those facilities. The compositions are particularly useful for objects found in health care facilities, including but not limited to, medical devices and equipment, for example, operating tables and other fixtures in operating rooms, hospital beds, tray tables, gurneys, wheelchairs, walkers, reusable medical devices and accessories, for example, instrument trays, scissors, stethoscopes, catheters, scalpels, lancets, stethoscopes, pacemakers, pacemaker cables, tracheostomy tubes, thermometers, sutures or surgical clamps. Other exemplary objects include, but are not limited to bathroom objects and surfaces (e.g., floors, tubs, showers, mirrors, toilets, bidets, and bathroom fixtures), kitchen surfaces (e.g., counter tops, stoves, ovens, ranges, sinks, refrigerators, freezers, microwaves, appliances, tables, chairs, cabinets, drawers, and floors,)

The compositions and methods provided herein are applicable to a wide range or materials including, but not limited to ceramic, vinyl, no-wax vinyl, linoleum, melamine, glass, enamel, plastics, plastified wood, metal (e.g., stainless steel, or chromed surfaces) any painted or varnished or sealed surface, textiles, or rubber.

The compositions can also be applied to surfaces of objects that come into contact with food. These objects can include food preparation and processing equipment, for example, utensils, cutlery, mixing apparatuses, grinders, for example meat grinders, tumblers, blenders, liquifiers, fermentation tanks, storage tanks or refrigeration equipment. The compositions can also be applied to surfaces used for food preparation including countertops, cutting boards, sinks, and other work surfaces.

The compositions and methods described herein may also be used for the treatment of surfaces of food products, for example, plants and plant parts (e.g. seeds, vegetables, and fruits). Suitable plants and plant parts include raw agricultural commodities (i.e., non-processed products) and processed products, as well as food products containing animal protein, for example meat, fish or shellfish.

Figure 6:
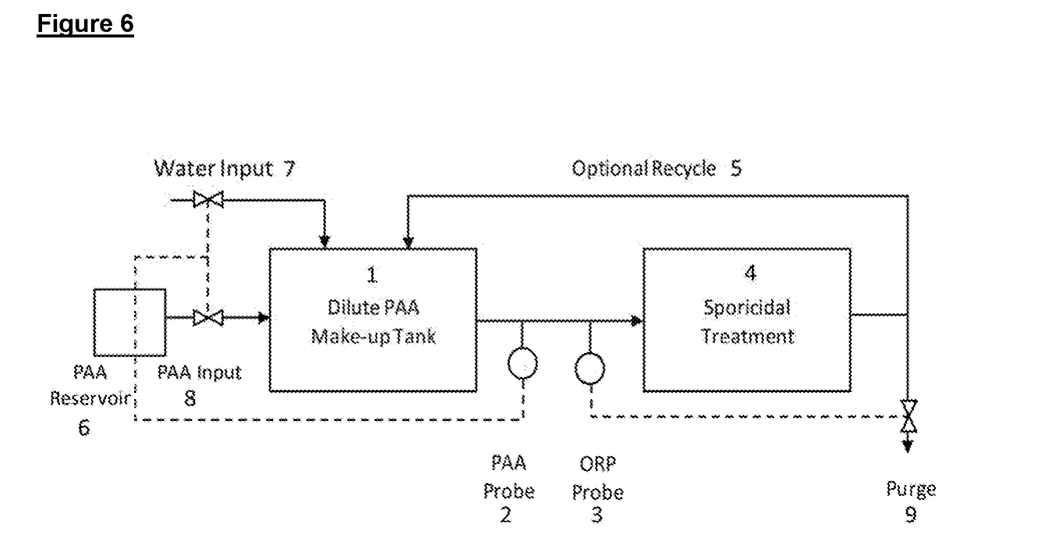
FIG. 6 is a schematic illustrating one embodiment of the treatment system.

Also provided are systems of reducing endospore contamination of a material based on the Applicant's finding that the antimicrobial efficacy of peracid-based systems is a function of oxidation power as indicated by the ORP. An exemplary system for carrying out the method of the claims is shown in FIG. 6. By monitoring the ORP, both PAA concentration and the optimum $PAA/H_2O_2$ ratio can be maintained.

The system provides one or more Make-up tanks 1 for diluting concentrated PAA which is fed from a PAA reservoir 6 via a PAA input 8, with water from a water input 7, a PAA probe 2 and an ORP probe 3 to monitor the discharge from the Make-up tank 1, and a sporicidal treatment tank 4 into which the diluted PAA is fed. The system can include an Optional Recycle line 5 to permit the use of the PAA after treatment It is expected that due to degradation PAA to $H_2O_2$, that the $H_2O_2$ concentration will be higher in the recycled solution than in the stock solution. To maintain an optimum $PAA/H_2O_2$ ratio, the ORP probe continuously monitors the ORP of the feed solution. The purge 9 can be adjusted accordingly. The PAA probe is used to monitor and control the input of PAA concentrate and water to a target level of PAA. Alternatively, an $H_2O_2$ probe can be used in lieu of or in addition to the ORP probe to monitor the $PAA/H_2O_2$ ratio.

EXAMPLES

Example 1

Microorganisms.

All microorganisms were purchased from certified manufacturers in spore form. The organisms and manufacturers are listed below.

*Paenibacillus chibensis*—American Type Culture Collection (ATCC);
*Paenibacillus favisporus*—DSMZ;
*Bacillus cereus* 14579—Presque Isle Cultures;
*Bacillus atrophaeus* 9372—Mesa Labs;
*Bacillus subtilis* 6633—Presque Isle Cultures;
*Bacillus subtilis* 19659—Presque Isle Cultures.

Upon receipt, the titer of the spore culture was assayed by serial dilution in Butterfield's buffer followed by plating on 3M AC Petrifilm™. The Petrifilm™ was then incubated at 35° C. for about 48 hours and enumerated. Cultures were stored in a dedicated refrigerator. Prior to each use, the titer of the spore culture was re-assayed to confirm that the culture remained viable and uncontaminated.

Example 2

*Paenibacillus chibensis* BAA-725 were treated with PAA formulations having ratios of $PAA/H_2O_2$ as shown in Table 1.

TABLE 1

| $PAA/H_2O_2$ Formulations | | | | | | | |
|---|---|---|---|---|---|---|---|
| Formulation | 1 | 2 | 3 | 4 | 5 | 6 | 7 |
| Nominal PAA, wt % | 5 | 15 | 15 | 22 | 35 | 15 | 22 |
| Nominal $H_2O_2$, wt % | 23 | 23 | 10 | 10 | 7 | 3 | 4 |
| $PAA/H_2O_2$ ratio | 0.2 | 0.6 | 1.5 | 2.2 | 5.0 | 5.0 | 5.0 |

The PAA formulations were diluted to about 2900 ppm in deionized water prior to use. The temperature of the formulations was raised to 55° C. and the actual PAA and $H_2O_2$ concentrations were measured in an autotitrator immediately before use.

*P. chibensis* BAA-725 were inoculated onto stainless steel strips. The *P. chibensis* BAA-725 contacted by submerging the strips into the PAA formulation for 10, 20, or 30 seconds. Any surviving organisms were recovered, incubated and counted. Microorganisms were recovered by suspending the culture in Letheen broth containing 0.5% sodium thiosulfate, sonicating for 5 minutes and vortexing for 30 seconds. The samples were then serially diluted in Butterfield's buffer, plated on 3M AC Petrifilm™, and incubated at 35° C. for about 48 hours. Following incubation, surviving microorganisms on the Petrifilm were counted.

The efficacy of spore killing was expressed as the D-value. The D-value is the time (e.g., seconds) needed for achieving a 1 $Log_{10}$ (or 90%) reduction of the target organism at the given temperature and PAA concentration. Thus, the smaller the D-value, the higher the efficacy of spore killing.

Figure 1:
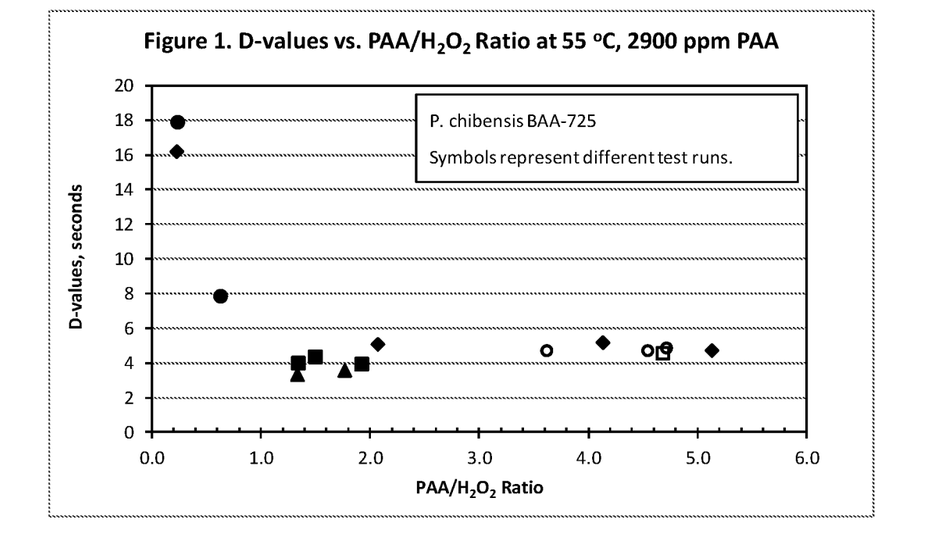
FIG. 1 is a graph showing the D-value as a function of the PAA/$H_2O_2$ ratio for *P. chibensis* BAA-725 at 2900 ppm of PAA at 55° C.

As shown in FIG. 1, the D-value decreased from about 16-18 seconds to about 4 seconds as the $PAA/H_2O_2$ ratio increased from 0.2 to 1.2. The D-value remained relatively constant at $PAA/H_2O_2$ ratios from about 1.8 to about 5.0. These data suggested that a useful $PAA/H_2O_2$ ratio for killing *P. chibensis* BAA-725 spores was above about 1.2.

Example 3

*Paenibacillus chibensis* BAA-725 were treated with a PAA formulations in the presence and absence of catalase, an enzyme that hydrolyzes $H_2O_2$.

An equilibrium $PAA/H_2O_2$ solution having 35 weight % PAA and 7 weight % $H_2O_2$ was diluted with deionized (DI) water to a PAA concentration of about 2900 ppm. For catalase treatment, 1 microliter of catalase (Sigma-Aldrich, Catalase from *Aspergillus,* 4000 units/mg protein, about 14.4 mg/ml of protein) was added to 200 ml solution and incubated at temperature for 45 minutes. Then the solution was warmed to 55° C. in a water bath. The warming step took about 38 minutes. Once the targeted temperature was reached, the actual PAA and $H_2O_2$ concentrations were measured with an autotitrator.

*P. chibensis* BAA-725 were inoculated onto stainless steel strips according to the method described in Example 1 and contacted with the catalase digested PAA solution and a control PAA solution that had not been catalase digested. The samples were treated with the PAA solutions for 10, 20, and 30 seconds.

The D-values were calculated as described above. The results of this analysis are shown in Table 2.

TABLE 2

D-value comparison of PAA solution with and without catalase enzyme

| Catalase | PAA/$H_2O_2$ ratio | D-value, seconds (P. Chibensis BAA-725) |
|---|---|---|
| No | 4.7 | 4.5 |
| Yes | 104.2 | 4.6 |

As shown in Table 2, the D-value obtained with a PAA solution at a PAA/$H_2O_2$ ratio of 4.7 was very similar to that obtained with the same PAA solution that had been treated with catalase to reduce the $H_2O_2$ content to less than 100 ppm. These data suggested that a PAA solution at a PAA/$H_2O_2$ ratio of 4.7 was at least as effective in killing *P. chibensis* BAA-725 as PAA samples that had been subjected to more time-consuming enzymatic treatment. These data further suggested that such enzymatic treatment was not needed for effective spore killing.

Example 4

*Paenibacillus favisporus* were treated with PAA formulations having ratios of PAA/$H_2O_2$ as shown in Table 3.

TABLE 2

PAA/$H_2O_2$ Formulations

| Formulation | 1 | 2 | 3 | 4 | 5 |
|---|---|---|---|---|---|
| Nominal PAA, wt % | 5 | 15 | 15 | 35 | 15 |
| Nominal $H_2O_2$, wt % | 23 | 23 | 10 | 7 | 3 |
| PAA/$H_2O_2$ ratio | 0.2 | 0.6 | 1.5 | 5.0 | 5.0 |

The PAA formulations were diluted to about 2900 ppm in deionized water prior to use. The temperature of the formulations was raised to 55° C. and the actual PAA and $H_2O_2$ concentrations were measured in an autotitrator immediately before use.

*P. favisporus* were inoculated onto stainless steel strips. The *P. favisporus* samples were contacted by submerging the strips into the PAA formulation for 10, 20, or 30 seconds. Any surviving organisms were recovered, incubated and counted. The efficacy of spore killing was expressed as the D-value.

Figure 2:
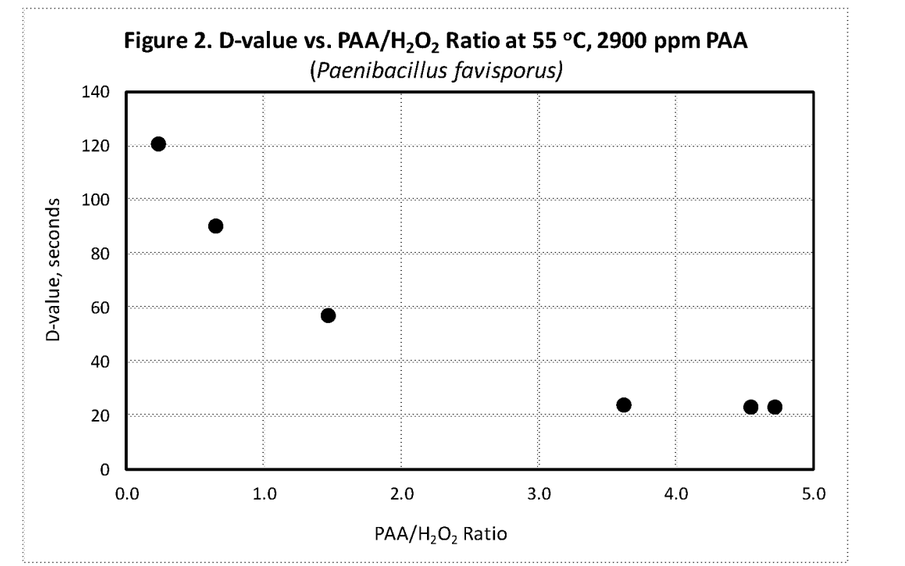
FIG. 2 is a graph showing the D-value as a function of the PAA/$H_2O_2$ ratio for *P. favisporus* at 2900 ppm of PAA at 55° C.

As shown in FIG. 2, the D-value decreased from about 120 seconds to about 20 seconds as the PAA/$H_2O_2$ ratio increased from 0.2 to about 3.5. The D-value remained relatively constant at PAA/$H_2O_2$ ratios from about 3.5 to about 4.5. These data suggested that a useful ratio for killing *P. favisporus* was about 3.5. These data also indicated that *P. favisporus* was more challenging to kill than was *P. chibensis* BAA-725.

Example 5

We evaluated the effect of PAA concentration and incubation temperature on the efficacy of PAA/$H_2O_2$ against *P. favisporus* spores.

Aliquots of an equilibrium PAA/$H_2O_2$ solution having 35 weight % PAA and 7 weight % $H_2O_2$ was diluted with deionized (DI) water to PAA concentration of about 2900 ppm, 4500 ppm, or 6000 ppm. The temperature of the formulations was raised to either 55° C. or 65° C. and the actual PAA and $H_2O_2$ concentrations were measured in an autotitrator immediately before use.

*P. favisporus* were inoculated onto stainless steel strips. The *P. favisporus* contacted by submerging the strips into the PAA formulation for 10, 20, or 30 seconds. Any surviving organisms were recovered, incubated and counted. The efficacy of spore killing was expressed as the D-value. The results of this experiment are shown in Table 3.

TABLE 3

Effect of PAA concentration and temperature on D-values for *P. favisporus*

| Temperature, ° C. | PAA concentration ppm | PAA/$H_2O_2$ ratio | D-value, seconds (P. Favisporus) |
|---|---|---|---|
| 55 | 2900 | 4.7 | 38 |
|  | 4500 | 4.4 | 22 |
|  | 6000 | 4.6 | 14 |
| 65 | 6000 | 4.6 | 6 |

As shown in Table 3, the D-value decreased from about 38 seconds to about 14 seconds as the PAA concentration increased from 2900 ppm to 6000 ppm PAA at a PAA/$H_2O_2$ ratio of between about 4.7 to about 4.6 at temperatures of 55° C. When the temperature was raised to 65° C., the D-value at 6000 ppm PAA at a ratio of about 4.6 decreased to 6.

Example 6

*P. favisporus* were treated with a PAA formulations in the presence and absence of catalase, an enzyme that hydrolyzes $H_2O_2$. The formulations are shown in Table 4.

TABLE 4

PAA/$H_2O_2$ Formulations

| Formulation | 1 | 2 | 3 | 4 | 5 |
|---|---|---|---|---|---|
| Nominal PAA, wt % | 15 | 15 | 22 | 35 | 15 |
| Nominal $H_2O_2$, wt % | 23 | 10 | 10 | 7 | 3 |
| PAA/$H_2O_2$ ratio | 0.6 | 1.5 | 2.2 | 5.0 | 5.0 |

The PAA solution was diluted with deionized (DI) water to a PAA concentration of about 6000 ppm. For catalase treatment, between 1 to 15 microliters of catalase (Sigma-Aldrich, Catalase from *Aspergillus*, 4000 units/mg protein) were added to 200 ml PAA solutions and incubated at room temperature for 45 minutes. Then the solutions were incubated in a 65° C. water bath for about 40 to about 70 minutes to reach the targeted temperature.

Once the targeted temperature was reached, the actual PAA and $H_2O_2$ concentrations were measured with an autotitrator.

*P. favisporus* were inoculated onto stainless steel strips according to the method described in Example 1 and contacted with the catalase digested PAA solution and a PAA solution that had not been catalase digested. The *P. favisporus* samples were contacted with PAA by submerging the strips into the PAA formulations for 10, 20, or 30 seconds. Any surviving organisms were recovered, incubated and counted. The efficacy of spore killing was expressed as the D-value. The results of this analysis are shown in FIG. 3.

Figure 3:
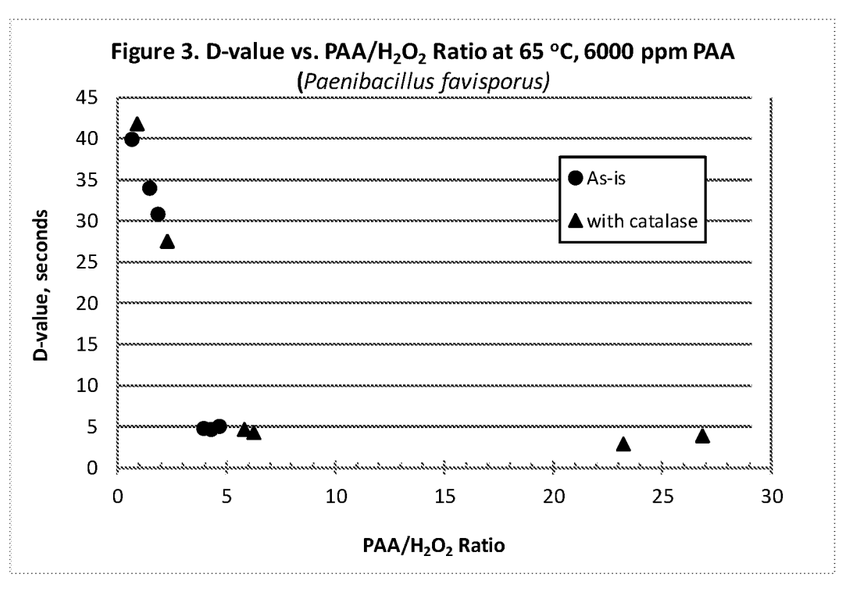
FIG. 3 is a graph showing the D-value as a function of the PAA/$H_2O_2$ ratio for *P. favisporus* at 6000 ppm of PAA at 65° C.

As shown in FIG. 3, the D-values for the PAA solution at 6000 ppm of PAA at 65° C. decreased from about 40 seconds to about 5 seconds as the PAA/$H_2O_2$ ratio increased from 0.2 to about 5.0. The D-values for the same solutions that had been catalase treated showed a similar trend, with a decrease from more than 40 seconds to about 6 seconds as the nominal PAA/$H_2O_2$ ratio increased from 0.2 to about 5.0. These data suggested catalase treatment did not increase the efficacy of PAA sporicidal activity.

Example 7

We evaluated the effect of PAA/$H_2O_2$ formulations on *Bacillus cereus* 14579, *Bacillus atrophaeus* 9372, *Bacillus subtilis* 6633, and *Bacillus subtilis* 19659 spores. The formulations are shown in Table 5.

TABLE 5

PAA/$H_2O_2$ Formulations

| Formulation | 1 | 2 |
|---|---|---|
| Nominal PAA, wt % | 5 | 5 |
| Nominal $H_2O_2$, wt % | 3 | 15 |
| PAA/$H_2O_2$ ratio | 1.6 | 0.3 |

The PAA formulations were diluted to about 1500 ppm in deionized water prior to use. The temperature of the formulations was raised to 50° C. and the actual PAA and $H_2O_2$ concentrations were measured in an autotitrator immediately before use.

The *Bacillus cereus* 14579, *Bacillus atrophaeus* 9372, *Bacillus subtilis* 6633, and *Bacillus subtilis* 19659 spores were inoculated onto stainless steel strips. The *P. favisporus* samples were contacted by submerging the strips into the PAA formulation for 10, 20, or 30 seconds. Any surviving organisms were recovered, incubated and counted. The efficacy of spore killing was expressed as the D-value. The results of this analysis are shown in Table 6.

TABLE 6

Effect of PAA concentration on D-values for *Bacillus* species

| | | D-value, seconds | | | |
|---|---|---|---|---|---|
| Formulation | PAA/$H_2O_2$ ratio | *B. cereus* | *B. atrophaeus* | *B. subtilis* 6633 | *B. subtilis* 19659 |
| 1 | 1.7 | 1.6 | 4.0 | 2.0 | 4.7 |
| 2 | 0.3 | 2.7 | 4.6 | 2.1 | 5.4 |

As shown in Table 6, both formulations showed sporicidal activity at 1500 ppm PAA at 50° C. against all the *Bacillus* species tested.

Example 8

We analyzed the oxidation-reduction potential (ORP) of aqueous PAA solutions. The solutions are shown in Table 7.

TABLE 7

PAA/$H_2O_2$ Formulations

| Formulation | 1 | 2 | 3 | 4 |
|---|---|---|---|---|
| Nominal PAA, wt % | 15 | 15 | 15 | 5 |
| Nominal $H_2O_2$, wt % | 6 | 10 | 23 | 23 |
| PAA/$H_2O_2$ ratio | 2.5 | 1.5 | 0.6 | 0.2 |

For analysis, the PAA formulations were serially diluted up to about 6000 ppm in DI water. The ORP was measured with an Accumet ORP probe with a Pt tip and an Accument Ag/AgCl reference electrode. The actual PAA and $H_2O_2$ concentrations were measured in an autotitrator. All solutions were at room temperature.

Figure 4:
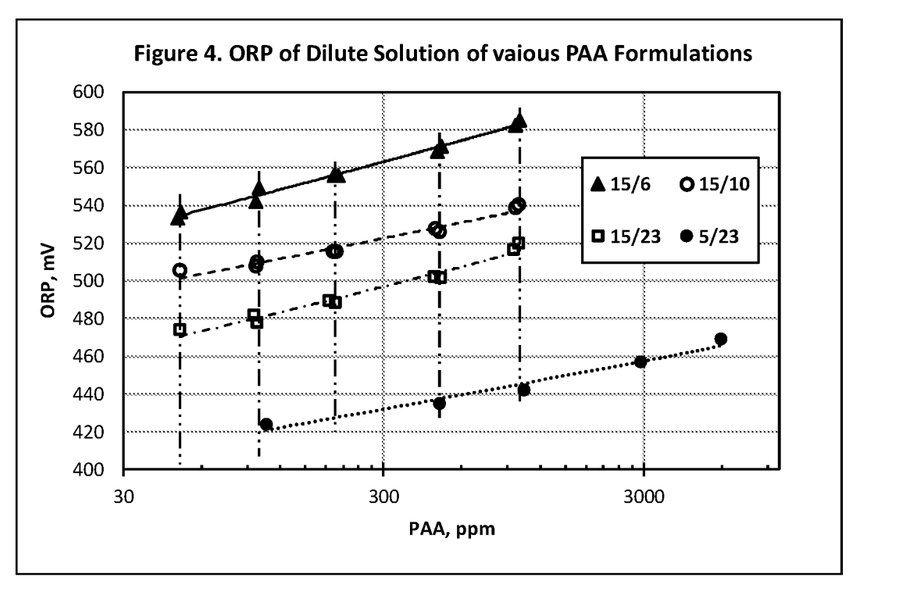
FIG. 4 is a graph showing the oxidation-reduction potential (ORP) as a function of the PAA concentration of various PAA formulations.

The relationship between ORP and the PAA concentration for the PAA formulations is shown in FIG. 4. As shown in FIG. 4, the ORP increased with increasing PAA concentration for each of the formulations. Surprisingly, ORP also increased as the PAA/$H_2O_2$ ratio increased even when the PAA concentration was held constant. For example, at about 90 ppm of PAA, the ORP was about 420 mV for a PAA/$H_2O_2$ ratio of 0.2 (Formulation 4 in Table 7). The ORP increased to about 480 mV for a PAA/$H_2O_2$ ratio of 0.6 (Formulation 3 in Table 7). The ORP increased to about 520 mV for a PAA/$H_2O_2$ ratio of 1.5 (Formulation 2 in Table 7). Finally, the ORP increased to about 540 mV for a PAA/$H_2O_2$ ratio of 2.5 (Formulation 1 in Table 7). This relationship held even for the highest PAA concentrations analyzed (500 ppm). At 500 ppm of PAA, the ORP was 440 mV, 500 mV, 540 mV, and 580 mV at PAA/$H_2O_2$ ratios of 0.2, 0.6, 1.5, and 2.5, respectively. These data suggested that increasing the $H_2O_2$ concentration in a PAA solution would adversely impact the ORP and thus the oxidation power of the solution. These data are consistent with those in the previous examples in which PAA formulations having higher PAA/$H_2O_2$ ratios had better sporicidal efficacies than did PAA formulations having lower PAA/$H_2O_2$ ratios.

Without being limited to any particular theory, it appears that the relationship between ORP and PAA/$H_2O_2$ ratios relates to the dual role played by $H_2O_2$ in the formulations.

Example 9

We evaluated the effect of an adjuvant on the ORP of aqueous PAA solutions. The solutions are shown in Table 8.

TABLE 8

PAA/$H_2O_2$ Adjuvant Formulations

| Formulation | 1 | 2 |
|---|---|---|
| Nominal PAA, wt % | 15 | 15 |
| Nominal $H_2O_2$, wt % | 10 | 10 |
| PAA/$H_2O_2$ ratio | 1.5 | 1.5 |
| $H_2SO_4$, wt % | None | 0.3 |

For analysis, the PAA formulations were serially diluted up to about 1000 ppm in DI water. The ORP was measured with an Accumet ORP probe with a Pt tip and an Accument Ag/AgCl reference electrode. The actual PAA and $H_2O_2$ concentrations were measured in an autotitrator. All solutions were at room temperature.

Figure 5:
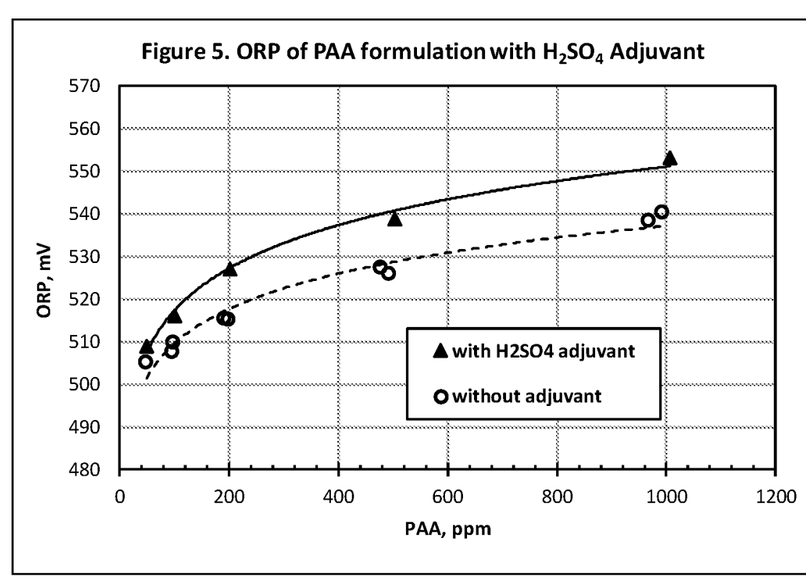
FIG. 5 is a graph showing the oxidation-reduction potential (ORP) as a function of the PAA concentration in the presence of $H_2SO_4$ adjuvant.

The relationship between ORP and the PAA concentration for the PAA formulations is shown in FIG. 5. As shown in FIG. 5, the ORP increased with increasing PAA concentration for each of the formulations. The ORP also increased in the presence of $H_2SO_4$ adjuvant.

Example 10

We analyzed the effect of $PAA/H_2O_2$ ratio on antimicrobial efficacy against the non-spore forming bacteria, *E. coli* and *Salmonella*.

*Escherichia coli* 8739 and *Salmonella enterica* 14028 were used in the experiments. 10 μL of inoculated suspension was placed using a pipet onto sterile stainless-steel foil strips and allowed to dry completely. Peracid test solutions were diluted to specified concentrations. 50 mL of PAA solutions were added to each sterile centrifuge tube respectively. Dried strips were dipped into the peracid solutions as described above. *Salmonella* were treated at 22° C.

The strips were then neutralized in 10 mL Letheen broth plus 0.5% sodium thiosulfate. The centrifuge tubes were capped and shaken. Neutralized tubes were sonicated for 5 minutes, and then vortexed for 30 seconds. Samples were serially diluted in Butterfield's buffer, plated on Petrifilm APC, and incubated at 35° C. for 48 hours.

As shown in Table 9, higher ratios of $PAA/H_2O_2$ had a better efficacy resulted in a decrease in the D-values for both *E. coli* and *Salmonella*.

TABLE 9

Effect of $PAA/H_2O_2$ ratio on D-values for *E. coli* and *Salmonella* species

| PAA grades | Nominal PAA/ $H_2O_2$ ratio | Test solution PAA (ppm) | *E. coli* Control, Log$_{10}$ | *E. coli* D-value, seconds | *Salmonella* Control, Log$_{10}$ | *Salmonella* D-value, seconds |
|---|---|---|---|---|---|---|
| 5% PAA | 0.2 | 200 | 4.4 | 3.6 | 5.1 | 3.0 |
| 35% PAA | 4.9 | 200 | 4.4 | 2.5 | 5.1 | 2.2 |

Example 11

We evaluated the effect of $PAA/H_2O_2$ ratio on PAA usage. *Bacillus atrophaeus* 9372 treated with PAA formulations as described above.

As shown in Table 8, the 22/10 PAA formulation at 1000 ppm PAA and 55° C. had a D-value (1.9 seconds) at approached the D-value (1.4 seconds) of the 5/15 PAA formulation at 1500 ppm at 60° C. In contrast, the D value for the 5/15 PAA formulation at 1500 ppm and 50° C. was 4.6 seconds. Thus, the amount of PAA used could be reduced by one third, while maintaining antimicrobial efficacy, by replacing the 5/15 PAA formulation at a low $PAA/H_2O_2$ ratio with a 22/10 PAA formulation at a high $PAA/H_2O_2$ ratio.

TABLE 10

Effect of $PAA/H_2O_2$ ratio on PAA usage

| PAA grades & $PAA/H_2O_2$ ratio | Test solution PAA, ppm | Temp. | Control Log$_{10}$ | Remaining counts after treatment time, Log$_{10}$ | | | D-values, sec |
|---|---|---|---|---|---|---|---|
| | | | | 5 sec | 8 sec | 12 sec | |
| 5/15 PAA; 0.3 | 1500 | 50° C. | 5.8 | 4.5 | 3.9 | 3.0 | 4.6 |
| 5/15 PAA; 0.3 | 1500 | 60° C. | 5.8 | 2.0 | 0.0 | 0.0 | 1.4 |
| | | | | 5 sec | 10 sec | 15 sec | |
| 22/10 PAA; 2.2 | 1000 | 55° C. | 6.1 | 3.7 | 0.6 | 0 | 1.9 |

From the foregoing, it will be appreciated by those skilled in the art that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method of treating a substrate for endospore contamination, the method comprising:
   a) preparing a solution comprising peracetic acid and hydrogen peroxide at a weight percent ratio of between 1.2 and 3.8;
   b) adjusting the concentration of the peracetic acid and hydrogen peroxide in the solution of step a) to provide an oxidation-reduction potential (ORP) of 500 mV to 1000 mV; and
   c) contacting the substrate with the solution of step b) for a time sufficient to reduce the endospore contamination, wherein the ORP is continuously monitored during the contacting step and wherein the solution of step b is applied to the substrate as a liquid, mist or fog;
   and wherein:
   peracetic acid is added during the monitoring of step c) to maintain the ORP at 500 mV to 1000 mV without the addition of hydrogen peroxide; and contact is maintained in step c) for up to 10 minutes.

2. The method of claim 1, wherein the method is performed in the absence of a peroxide decomposing enzyme.

3. The method of claim 1, wherein the endospores are produced by a microbe selected from the group consisting of *Paenibacillus chibensis, Paenibacillus favisporus, Bacillus cereus, Bacillus atrophaeus, Bacillus subtilis, Geobacillus stearothermophilus* and a combination thereof.

4. The method of claim 1, wherein the substrate comprises a material selected from the group consisting of metal, plastic, ceramic, glass, wood, rubber composite, and a combination thereof.

5. The method of claim 1, wherein the substrate comprises a medical device, food or beverage preparation equipment, pharmaceutical manufacturing equipment, or a foodstuff.

6. The method of claim 1, wherein the contacting in step c) is for 3 to 60 seconds.

7. The method of claim 6, wherein the solution of step a) comprises 500-7500 ppm of peracetic acid.

8. The method of claim 7, wherein the contacting in step c) is for 3 to 60 seconds.

9. The method of claim 1, wherein the contacting in step c comprises dipping, spraying, immersing or soaking.

10. The method of claim 1, wherein the oxidation-reduction potential (ORP) of the solution of step c) is 540 mV to 780 mV and peracetic acid is added during the monitoring of step c) to maintain the ORP in this range.

11. The method of claim 1, wherein the contacting in step c is for 30 seconds to 8 minutes.

12. The method of claim 1, wherein the endospore contamination is reduced by about 1 $\log_{10}$.

13. The method of claim 1, wherein the endospore contamination is reduced by about 90%.

14. The method of claim 3, wherein the substrate comprises a material selected from the group consisting of metal, plastic, ceramic, glass, wood, rubber composite, and a combination thereof.

15. The method of claim 14, wherein the substrate comprises a medical device, food or beverage preparation equipment, pharmaceutical manufacturing equipment, or a foodstuff.

16. The method of claim 15, wherein the method is performed in the absence of a peroxide decomposing enzyme.

17. The method of claim 16, wherein the contacting in step c) is for 3 to 60 seconds.

18. The method of claim 15, wherein the contacting in step c) is for 3 to 60 seconds.

19. The method of claim 18, wherein the contacting in step c comprises dipping, spraying, immersing or soaking.

20. The method of claim 1, wherein the solution of step a), comprising peracetic acid and hydrogen peroxide, further comprises an adjuvant.

* * * * *